United States Patent
Wagner et al.

(10) Patent No.: US 6,631,829 B1
(45) Date of Patent: Oct. 14, 2003

(54) DEVICE FOR DISCHARGING FLOWABLE MATERIALS AND METHOD OF USING SAME

(75) Inventors: Ingo Wagner, Herrsching (DE); Gerd Brandhorst, Landsberg (DE); Martin Beuschel, München (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 09/869,112

(22) PCT Filed: Dec. 22, 1999

(86) PCT No.: PCT/EP99/10316
§ 371 (c)(1),
(2), (4) Date: Jun. 25, 2001

(87) PCT Pub. No.: WO00/38841
PCT Pub. Date: Jul. 6, 2000

(30) Foreign Application Priority Data

Dec. 23, 1998 (DE) ..................... 298 22 967 U

(51) Int. Cl.⁷ ................................. B67D 5/06
(52) U.S. Cl. ......................... 222/23; 222/327
(58) Field of Search .............. 222/23, 52, 95, 222/105, 327

(56) References Cited

U.S. PATENT DOCUMENTS

| 3,612,321 A | * | 10/1971 | Larson ........................ 215/365 |
| 5,031,797 A | * | 7/1991 | Boris et al. ................... 222/23 |
| 5,286,105 A | | 2/1994 | Herold et al. ................. 366/177 |
| 5,312,017 A | * | 5/1994 | Schroeder et al. ............ 222/23 |
| 5,488,447 A | * | 1/1996 | Patton et al. .................. 396/578 |
| 5,507,412 A | * | 4/1996 | Ebert et al. .................... 222/63 |
| 6,039,430 A | * | 3/2000 | Helterline et al. ............ 347/19 |
| 6,264,066 B1 | * | 7/2001 | Vincent et al. ................ 222/95 |

FOREIGN PATENT DOCUMENTS

| DE | 39 19 105 A1 | 8/1992 |
| EP | 0 699 582 A1 | 3/1996 |
| EP | 0 791 403 A1 | 8/1997 |

* cited by examiner

Primary Examiner—Paul J. Hirach
Assistant Examiner—Melvin A. Cartagena
(74) Attorney, Agent, or Firm—Crowell & Moring LLP

(57) ABSTRACT

When dispensing a flowable substance from a container by way of a motor driven dispensing device, for ensuring that the container is properly inserted into the device, that the substance is still usable and/or that the dispensing speed is selected in accordance with the viscosity or other properties of the substance, the container is provided with a marking which may be stored in a transponder provided at a front container cap. When the container is properly inserted into the dispensing device, the transponder cooperates with a sensor disposed in an end wall of the device for enabling and/or controlling the dispensing mechanism on the basis of the characteristic data detected.

14 Claims, 2 Drawing Sheets

Figure 1:
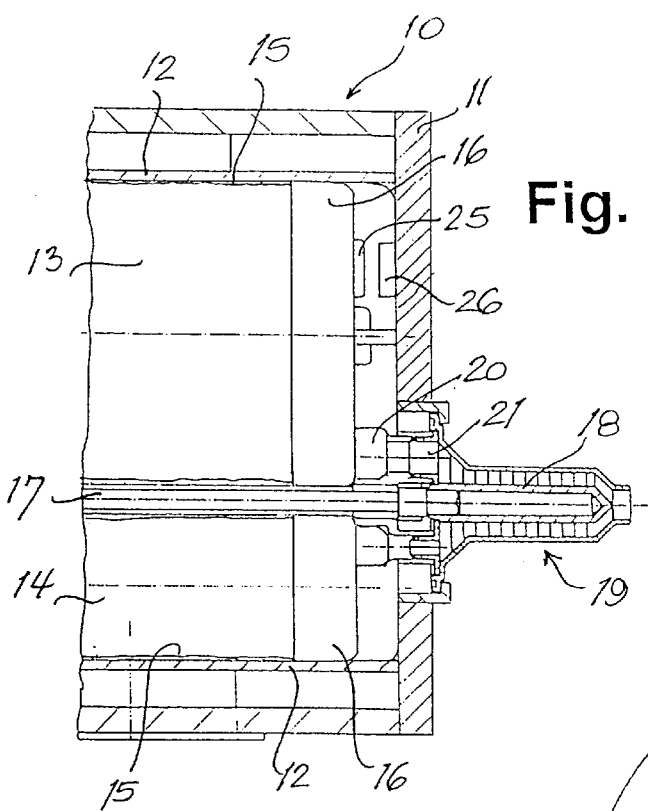

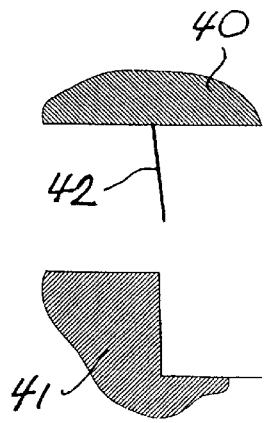
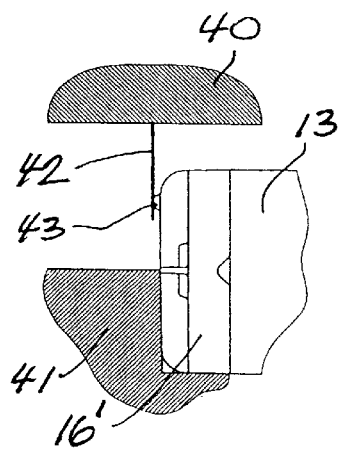
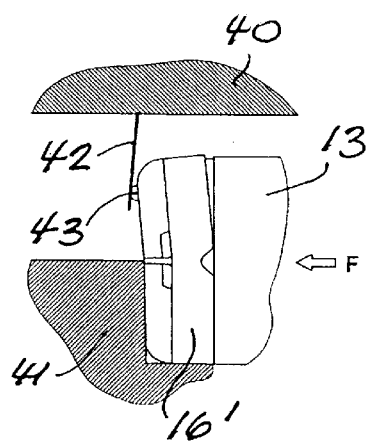
Fig. 5a     Fig. 5b     Fig. 5c
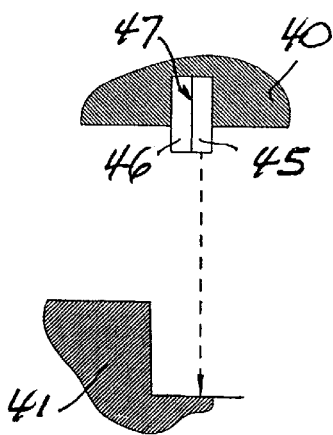
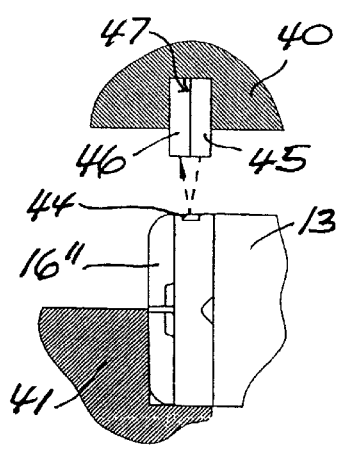
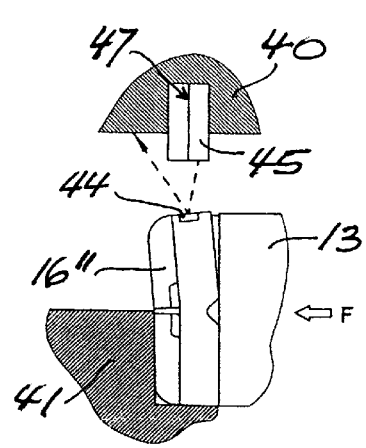
Fig. 6a     Fig. 6b     Fig. 6c

DEVICE FOR DISCHARGING FLOWABLE MATERIALS AND METHOD OF USING SAME

A device for dispensing flowable substances, having the features recited in the preamble of claim 1, is known from EP 0 492 413 A1. There is provided a shell-shaped receptacle for receiving two cartridges in parallel, each cartridge having, at its rear end, a dispensing piston and, at its front end, an opening to be coupled to a rear entry opening of a mixer provided on the device. During dispensing, both pistons are synchronously advanced by an electrical motor which also drives a rotor within the mixer.

The advancing speed of the pistons and, possibly, also the driving speed of the mixer rotor can depend upon the properties of the substances contained in the cartridges, to such as viscosity or sensitivity to mechanical forces. The proper dispensing parameters are to be selected by the operator. Setting unsuitable parameters may lead to undesired changes of the substance being dispensed or damages to the device.

Some substances have properties that change over time and are therefore to be used prior to an expiry date determined by the producer. This is particularly true with components which react with each other and are mixed together for producing a ready-to-use substance. If the operator fails to pay attention to the expiry date, the substance dispensed from the device may be unusable or at least deteriorated in its properties.

Finally, it is essential for each cartridge to be properly inserted into the receptacle of the device. If this is not done, entry of the piston into the cartridge and/or engagement of the mixer shaft in the mixer is not properly ensured, which may cause damage to the device, lead to unmixed substances being dispensed, or result in leakage. Again, one relies on the operator to insert the cartridges properly.

DE 39 19 105 A1 discloses a gluing machine in which cartridges are filled with adhesive components in a predetermined mixing ratio. A visible marking tells the operator whether the machine has been properly filled in accordance with the mixing ratio. There is also mention of a "pneumatic" encoding and inhibition of the gluing machine if wrong cartridges are inserted.

It is the object of the invention to prevent such a dispensing device from being improperly handled, specifically from having a container improperly inserted or an unsuited container being inserted, possibly also an unsuited mixer being used.

The invention is characterized in claim 1 provides a solution to this object. According to claim 1, a marking provided on the container and its detection by means provided in the device make sure that the emptying mechanism of the device functions only if the marking has been recognized as admissible, and possibly operates in response to the contents of the marking. The marking may contain information concerning the properties of the container content, its durability, the producer, and other data. Since the marking and the detecting means must be related to each other, it becomes possible to make sure that the marking is recognized as valid only if the container is in a predetermined position within the receptacle of the device.

Preferred embodiments of the marking and of the detecting means cooperating therewith are recited in claims 2 to 6.

The embodiments of the invention set forth in claims 7, 8 and 16 relate to a preferred location of the marking and detecting means on the container and on the device, respectively.

It is of particular advantage to use the marking for establishing not only the proper position of the container but also the proper operation of the device, as in the embodiment of the invention according to claims 9 and 10.

The embodiment of claim 11 is specifically related to the detection of the internal pressure of the container which, under certain conditions, may become excessive during dispensing. To this end, it is specifically a deformation of the container cap that is detected, which deformation may occur if it is attempted to dispense improper or too old and taut pastes whereby a certain maximum dispensing force is exceeded. It thus becomes possible to avoid damage to the dispensing device, contamination of the device due to breakage of a container, or other risks. There is thus not only detection as to whether a container suited for the device has been properly inserted; overload conditions during dispensing are also prevented. This avoids the need for an expensive overload clutch, as is provided with some prior-art devices.

Embodiments of the marking and detecting means which are advantageous for this use are recited in claims 12 to 15.

The embodiment of the invention according to claims 17 and 18 is of advantage in that it ensures the use of a proper mixture in a mixing and dispensing device for mixtures of two or more components.

The feature of claim 19 is advantageous in that certain information contained in the marking, such as the expiry date, are immediately recognizable to the user.

Figure 2:
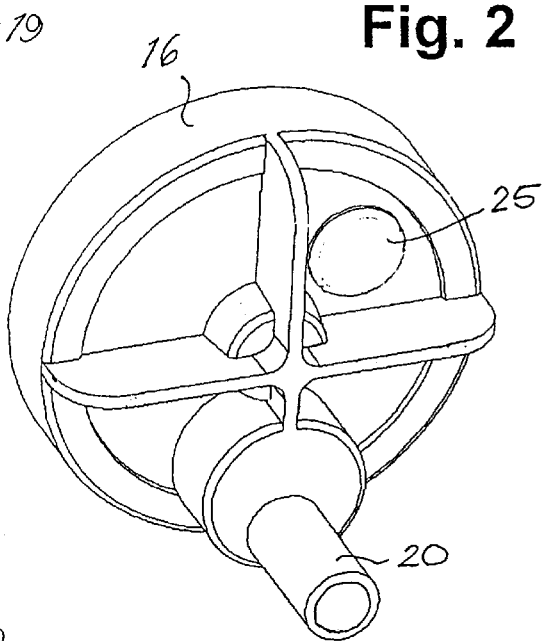
Figure 3:
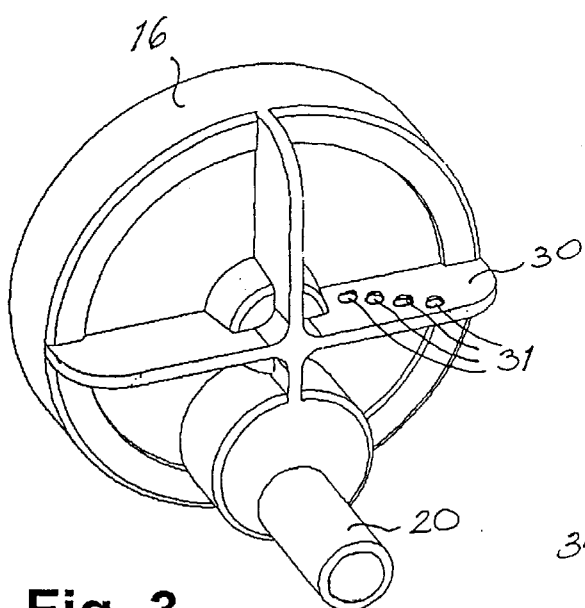
Figure 4:
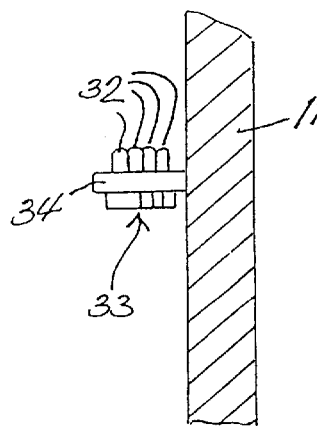

Preferred embodiments of the invention will be described below with reference to the drawing, in which FIG. 1 is a longitudinal section through the front part of a dispensing device, FIG. 2 is a perspective view of a cap which constitutes the front part of a container, FIG. 3 is a perspective view similar to FIG. 2 showing the container cap of a further embodiment, FIG. 4 illustrates part of a device adapted to the arrangement of FIG. 3, FIGS. 5a to 5c are schematic views of part of the dispensing device with means for detecting the container marking in accordance with a further embodiment, and FIGS. 6a to 6c are representations similar to FIGS. 5a to 5e, illustrating yet another embodiment.

The dispensing device shown in part in FIG. 1 includes a housing 10 having an end wall 11 and a receptacle 12 for receiving two substantially cylindrical containers 13, 14 in parallel.

In the present case, each of the containers 13, 14 is constituted by a film tube 15 the front end of which is glued into a rigid cap 16. FIG. 1 shows various details only of the container 13, whereas the container 14 is shown only schematically. FIG. 2 is a perspective view of the cap 16.

The film tubes 15 of the two containers 13, 14, are emptied by pistons (not shown) which engage their rear ends and which are synchronously advances by an electrical motor (not shown). The motor also rotates a shaft 17 the front end of which is coupled to a rotor 18 of a dynamic mixer 19 connected to either the container caps 16 or the housing end wall 11. Either cap 16 has an outlet pipe 20 which leads into a corresponding inlet pipe 21 provided at the rear end of the mixer 19.

A transponder 25 is disposed at the front end of the cap 16, in which data are stored that are related to the container 13, its contents, the expiry date of the contents and/or the producer. A sensor 26 cooperating with the transponder 25 is disposed at a position of the housing end wall 11 exactly opposite the transponder 25. When the container 13 is in its prescribed position in which the transponder 25 is sufficiently close to the sensor 26, the data stored in the transponder 25 are received by the sensor 26 which enables the actuation of the dispensing device if these data correspond to those stored in a control of the device. The actual operation for driving the dispensing pistons and the mixer shaft 17 is initiated by a switch (not shown).

Where the data transmitted from the transponder 25 to the sensor 26 contain information on the substance in the container 13, the advancing speed of the dispensing pistons and/or the rotational speed of the mixer rotor 18 may be controlled correspondingly.

Additional means (not shown) may be provided to provide an indication of the data transmitted from the transponder 25, such as the expiry date. The indicating means may be in the form of a display on the device or on a separate screen.

The second container 14 shown in FIG. 1 may also be provided with a transponder, just as the container 13, the transponder cooperating with a sensor correspondingly positioned on the end wall 11 of the device housing 10. In this case, it may be ensured that both containers contain suitable components for producing the desired mixture.

In an alternative embodiment, only one of the two containers 13, 14 of the dispensing device shown in FIG. 1 may be provided with a transponder 25, and the device may be provided with a single sensor 26. Further, the transponder 25 and the sensor 26 may be located at positions other than those shown in the drawings.

The invention is not restricted to devices for producing substances from two or more components. A transponder 25 provided on a container 13, which holds a substance to be dispensed, and cooperating with a sensor 26 on the device is useful also in a pure dispensing device. In this case, the data stored in the transponder 25 may be used to control the dispensing speed and/or prevent the use of a substance that has expired.

Instead of the transponder 25 assumed in FIGS. 1 and 2, the marking of the container may be contained in a magnetic code or an optically readable bar code provided on the end wall of the cap 16, and the respective code may be sensed by a corresponding magnetic or optical code reader located at a position of the end wall 11 of the housing 10 corresponding to the sensor 26 in FIG. 1.

In yet another embodiment (not shown), the marking of the container or container contents may be provided in an electronic circuit chip again located at the position of the transponder 25 in FIG. 1 and cooperating with a corresponding sensor 26 provided on the end wall 11 of the housing 10. In this case, the sensor may include contact elements for the circuit chip and a processor connected to such contact elements.

In the second embodiment of the invention shown in FIGS. 3 and 4, recesses or holes 31 are provided on a rib 30 which projects in the forward direction from the cap 16. When the container 13 is completely inserted in the device, these recesses or holes 31 may be engaged by actuator pins 32 of microswitches 33 disposed on a web 34 that extends parallel to the rib 30 and projects rearward from the housing end wall 11.

In the embodiment shown, the rib 30 is provided with four holes 31 which cooperate with the actuator pins 32 of a total of four microswitches 33. In this case, when the container 13 is inserted from the above in FIG. 4, none of the microswitches 33 is actuated. If only some of the holes 31 are provided in the rib 30, only those microswitches 33 are actuated that have actuator pins 32 for which no hole is provided. Thus, different information is transmitted depending on the number of holes 31 provided in the rib 30.

Instead of the holes 31 provided in the rib 30 in the cap 16, as shown in FIGS. 3 and 4, other surface formations similar to a key bit may be provided in which data related to the container 13 or the container contents are coded. In this case, the housing 10 has corresponding spring elements to sense such surface formations and detect information corresponding to the configuration thereof.

In addition to, or instead of, the marking provided on the container, a marking (not shown) may be provided on the mixer which cooperates with the same or a separate evaluation unit provided on the device housing 10 in order to ensure that the appropriate mixer 19 is used in relation to the device and/or the substance to be dispensed. In this case, the device control is so arranged that it enables the operation of the device only if both markings coincide with the data provided in the control.

FIGS. 5a to 5c are schematic representations showing only a part of the peripheral wall 40 and a part of the end wall 41 of the container receptacle of a dispensing device. This device largely corresponds to that shown in FIG. 1 but differs therefrom in that a sensor 42 in the form of a pivotal rod extends from the peripheral wall 40 into the space receiving the container 13 (FIG. 5b).

In FIG. 5a, the sensor 42 is in a rest position biased to the right, which the sensor assumes when no container is placed in the dispensing device.

In the representation of FIG. 5b, a container 13 is in its normal operating position. The container 13 has a projection 43 at the end surface of its cap 16'. The projection 43 deflects the sensor 42 from the position shown in FIG. 5a along the piston advancing direction to the normal operating position. In this position of the sensor 42, the dispensing device is ready for operation.

If the container 13 is not properly inserted into the device or if it is a container which is not suited for use with the device and may cause malfunction, the sensor 42 is not deflected from its rest position, thereby disabling the dispensing operation.

FIG. 5c shows a case in which the cap 16' of the container 13 has become deformed due to excessive pressure so that the projection 43 deflects the sensor 42 beyond its normal operating position to an abnormal position. The dispensing process is interrupted in this position of the sensor 42.

Such a deformation of the housing cap 16' may occur if it is attempted to dispense improper or too old, thus taut pastes, so that a certain maximum dispensing pressure F is exceeded. Damage to the dispensing device, contamination of the device due to breakage of a container and other hazards are thus reliably prevented.

The abnormal position of the sensor 42 shown in FIG. 5c may be caused also by the use of an improper container which has an excessive projection at the end wall of the cap 16' in the area of the sensor 42.

The embodiment shown schematically in FIGS. 6a to 6c differs from that of FIGS. 5a to 5c in that the projection 43 at the cap 16" of the container 13 is replaced by a reflecting mark 44 which is sensed by a light barrier 47 comprising a light emitter 45 and a light receiver 46. In the rest position shown in FIG. 6a, in which no container has been inserted, the light beam emitted by the light emitter 45 is insufficiently reflected.

In the normal operating condition shown in FIG. 6b, the light beam is reflected by the reflecting mark 44 onto the light receiver 46, the output signal of which is supplied to an evaluation circuit (not shown) to enable the operation of the dispensing device.

If the container cap 16" is deformed due to overload, the light beam reflected by the reflecting mark 44 leaves the light receiver 46 which then generates no output signal. Such an abnormal condition is detected by the evaluation circuit which interrupts the dispensing process.

The embodiments of FIGS. 5a to 5c and 6a to 6c thus permit not only the detection as to whether a container suited for use in the device has been properly inserted, but also prevent overload conditions during dispensing. In some prior art devices, such an overload condition is prevented by a separate, expensive overload clutch in the drive mechanism, which the invention renders superfluous.

What is claimed is:

1. A device for dispensing flowable substances, comprising a housing for receiving a container containing the substance and having a marking element, and means for emptying the container,
   wherein the housing includes detecting means for detecting the marking element, the detecting means controlling the dispensing device in response to the output signal of the detecting means, and
   wherein the marking element is contained in an electronic circuit chip provided on the container and the detecting means includes a processor adapted to be placed in contact with the chip.

2. The device of claim 1, wherein the container includes a film tube and a cap provided at the front end of the film tube and carrying the marking element.

3. The device of claim 1, wherein the container is substantially cylindrical and adapted to be inserted into a container receptacle of the housing transverse to its longitudinal axis, the marking element being arranged on an end face extending transverse to the longitudinal axis, and the detecting means being disposed on a wall of the housing opposite this end face.

4. The device of claim 1, wherein the container is substantially cylindrical and adapted to be inserted into a container receptacle of the housing transverse to its longitudinal axis, the marking element being provided on a surface extending parallel to the longitudinal axis, and the detecting means being disposed on a wall of the housing opposite this surface.

5. A device for dispensing flowable substances, comprising a housing for receiving a container containing the substance and having a marking element, and means for emptying the container,
   wherein the housing includes detecting means for detecting the marking element, the detecting means controlling the dispensing device in response to the output signal of the detecting means,
   wherein the marking element is related to the spatial position of the container and the detecting means controls the dispensing device in response to the position of the marking element,
   wherein the detecting means differentiates between a rest position in which there is no container in the dispensing device, a working position in which a container including the marking element is in the proper position within the dispensing device, and an abnormal position in which the marking element is in a position indicating an improper position of the container in the dispensing device, and
   wherein the marking element is provided on a part which is displaceable in response to the internal pressure of the container.

6. The device of claim 5, wherein the detecting means is a mechanical sensor for sensing the marking element.

7. The device of claim 5, wherein the detecting means is a sensor for sensing the marking element in a non-contacting manner.

8. A device for dispensing flowable substances, comprising a housing for receiving a container containing the substance and having a marking element, and means for emptying the container,
   wherein the housing includes detecting means for detecting the marking element, the detecting means controlling the dispensing device in response to the output signal of the detecting means,
   wherein the marking element is related to the spatial position of the container and the detecting means controls the dispensing device in response to the position of the marking element,
   wherein the detecting means differentiates between a rest position in which there is no container in the dispensing device, a working position in which a container including the marking element is in the proper position within the dispensing device, and an abnormal position in which the marking element is in a position indicating an improper position of the container in the dispensing device,
   wherein the detecting means is a sensor for sensing the marking element in a non-contacting manner and detects the marking element passing through the working position when the container is inserted into the dispensing device.

9. A device for dispensing flowable substances, comprising a housing for receiving at least two containers each containing one substance and having a marking element, a mixer and means for emptying the container,
   wherein the housing includes detecting means for detecting the marking element, the detecting means controlling the dispensing device in response to the output signal of the detecting means, and
   wherein the mixer is provided with a marking element and the housing is provided with means for detecting the marking element.

10. The device of claim 9, wherein the marking element of the container and that of the mixer are detected by the same detecting means.

11. A device for dispensing flowable substances, comprising a housing for receiving a container containing the substance and having a marking element, and means for emptying the container,
   wherein the housing includes detecting means for detecting the marking element, the detecting means controlling the dispensing device in response to the output signal of the detecting means,
   wherein the marking element is related to the spatial position of the container and the detecting means controls the dispensing device in response to the position of the marking element,
   wherein the detecting means differentiates between a rest position in which there is no container in the dispensing device, a working position in which a container including the marking element is in the proper position within the dispensing device, and an abnormal position in which the marking element is in a position indicating an improper position of the container in the dispensing device, and
   wherein the marking element includes a reflecting mark and the sensor is a light barrier and detects the marking element passing through the working position when the container is inserted into the dispensing device.

12. A device for dispensing a flowable substance, comprising a housing for receiving a container containing the substance and having a marking element related to a spatial position of the container, means for emptying the container, and detecting means for detecting the marking element and controlling the dispensing device in response to an output signal of the detecting means, wherein the marking element is provided on a part which is displaceable in response to internal pressure of the container.

13. A device for dispensing a flowable substance, comprising a housing for receiving a substantially cylindrical container containing the substance and having a marking element, means for emptying the container, and detecting means for detecting the marking element and controlling the dispensing device in response to an output signal of the detecting means, wherein the container is adapted to be inserted into a container receptacle of the housing transverse to its longitudinal axis, the marking element being provided on an end face of the container extending transverse to said longitudinal axis, and the detecting means being disposed on a wall of the housing opposite said end face.

14. A device for dispensing flowable substances, comprising a housing for receiving a substantially cylindrical container containing the substance and having a marking element, means for emptying the container, and detecting means for detecting the marking element and controlling the dispensing device in response to an output signal of the detecting means, wherein the container is adapted to be inserted into a container receptacle of the housing transverse to its longitudinal axis, the marking element being provided on a surface of the container extending parallel to said longitudinal axis, and the detecting means being disposed on a wall of the housing opposite said surface.

* * * * *